(12) United States Patent
Fellinger (10) Patent No.: US 8,086,042 B2
(45) Date of Patent: Dec. 27, 2011

(54) WEATHERIZATION IMAGING SYSTEMS AND METHODS

(75) Inventor: Thomas J. Fellinger, Littleton, CO (US)

(73) Assignee: Johns Manville, Denver, CO (US)

( * ) Notice: Subject to any disclaimer, the term of this patent is extended or adjusted under 35 U.S.C. 154(b) by 1313 days.

(21) Appl. No.: 11/617,964

(22) Filed: Dec. 29, 2006

(65) Prior Publication Data

US 2008/0159616 A1   Jul. 3, 2008

(51) Int. Cl.
*G06K 9/68* (2006.01)
(52) U.S. Cl. .................................. 382/218; 382/141
(58) Field of Classification Search .................. 250/330; 378/63; 382/103, 141, 218; 702/136
See application file for complete search history.

(56) References Cited

U.S. PATENT DOCUMENTS

| | | | |
|---|---|---|---|
| 7,271,706 B2 * | 9/2007 | Lee | 340/384.2 |
| 7,321,119 B2 * | 1/2008 | King | 250/330 |
| 7,529,646 B2 * | 5/2009 | Lin et al. | 702/188 |
| 7,605,924 B2 * | 10/2009 | Howard et al. | 356/502 |
| 2003/0146975 A1 * | 8/2003 | Joung et al. | 348/164 |
| 2004/0183678 A1 * | 9/2004 | Jaffrey | 340/557 |
| 2005/0126441 A1 * | 6/2005 | Skelhorn | 106/409 |
| 2006/0043296 A1 * | 3/2006 | Mian et al. | 250/330 |
| 2008/0159616 A1 * | 7/2008 | Fellinger | 382/141 |
| 2009/0210192 A1 * | 8/2009 | Askar | 702/136 |

* cited by examiner

*Primary Examiner* — Gregory M Desire
(74) *Attorney, Agent, or Firm* — Robert D. Touslee (57) ABSTRACT

Methods and systems for evaluating a performance installment in a building construction include preparing a first image of the building construction, implementing the performance installment in the building construction, preparing a second image of the building construction subsequent to or during implementation of the performance installment, and evaluating the performance installment based on a comparison between the first image and the second image. Performance installments include weatherization measures such as the application of thermal insulation and air-sealing. Related methods and systems for calculating a performance plan for a building construction include transmitting analysis information to a processor, and determining the performance plan based on the analysis information. The analysis information may include a thermal signature, an airflow signature, an acoustic signature, or a vibrational signature.

20 Claims, 5 Drawing Sheets

WEATHERIZATION IMAGING SYSTEMS AND METHODS

BACKGROUND OF THE INVENTION

Embodiments of the present invention relate to systems and methods for evaluating weatherization techniques, and in particular to approaches for determining the quality and effectiveness of building insulation measures.

A variety of approaches can be used to weatherize or comfortize a building or structure. For example, it is possible to add insulation to wall, ceiling, and floor constructions to achieve a desired level of thermal, acoustic, or vibrational performance. Such insulation measures, which include drill and fill techniques, have long been employed by insulation contractors, re-modelers, and do-it-yourselfers. Drill and fill techniques typically involve drilling holes or cutting access slots into an un-insulated, under-insulated, or semi-insulated cavity of a given structure and then filling the cavity with pneumatically applied insulation or pressurized foam.

Although drill and fill techniques and other weatherization and comfortization procedures provide many benefits to a building or home, such methods may have heretofore been limited due to the lack of effective solutions for accurately gauging the adequacy of the procedure. For example, because the drill and fill technique is often a "blind" procedure where the installer cannot see the material being placed within the interior construction cavity, it is typically difficult for the contractor, the homeowner, or both, to know that the cavity has been adequately filled, that no voids or compressions are present, and that the correct insulation density exists in a uniform manner throughout one or more cavities, to provide a desired level of thermal and acoustic performance.

Current methods for gauging the adequacy of a drill and fill procedure involve counting the number of bags of insulation installed to estimate insulation coverage, installing insulation product under very high pressures to achieve high density, and using snake wires to check for voids in construction cavities. However, such methods are often prone to considerable error, and some can even cause damage to the building or structure.

For at least these reasons, there remains a need for improved systems and methods for evaluating a weatherization or comfortization installment in a building construction.

BRIEF SUMMARY OF THE INVENTION

Advantageously, embodiments of the present invention provide imaging techniques that evaluate the effectiveness of weatherization, comfortization, or other performance measures that are implemented in a building or structure. For example, before and after thermal images can be provided to homeowners to illustrate resultant heat flow reductions. Relatedly, images can be used as part of a computer program to map out cavities for drilling and determine how much insulation should be added to each cavity. In some embodiments, images can provide a map to show where air sealing is needed or desired. Before and after images can be used to show a homeowner the quality of a fill and drill procedure. It is also possible to use these techniques to show installation deficiencies that can be prepared prior to plugging drill and fill access holes. These techniques are well suited for providing or supporting energy savings guarantees. Also provided are methods and systems for implementing a performance installment in a building construction are provided herein. An exemplary implementation method includes imaging the building construction, calculating the performance installment based on the image, and implementing the performance installment.

In a first aspect, embodiments of the present invention provide a method of evaluating a performance installment in a building construction. The method can include, for example, preparing a first image of the building construction, implementing the performance installment in the building construction, preparing a second image of the building construction subsequent to or during implementation of the performance installment, and evaluating the performance installment based on a comparison between the first image and the second image. In some cases, the first image includes a first thermal image and the second image includes a second thermal image. The first image can represent a heat loss signature or a heat gain signature of the building construction. The building construction can include an exterior wall, an interior wall, a ceiling, a floor, a roof, an attic, a rafter, a basement, a crawlspace, or the like. The performance installment can include a thermal insulation installment, an air sealing installment, an acoustic installment, a vibrational installment, or the like. In some cases, the step of evaluating the performance installment involves inputting the first and second images into a computer and processing the first and second images with mapping software to provide a map of the building construction. Evaluation methods may also include inputting the first image into a computer and calculating a set of treatment parameters for the performance installment based on the first image. A set of treatment parameters can include a thermal insulation location, a thermal insulation density, a thermal insulation amount, an air sealing location, and the like. In some cases, an evaluation method includes incorporating a performance installment evaluation into an energy guarantee program.

In another aspect, embodiments of the present invention provide a method of calculating a performance plan for a building construction. The method may include, for example, transmitting analysis information to a processor, and determining the performance plan based on the analysis information. The analysis information may include a thermal signature, an airflow signature, an acoustic signature, a vibrational signature, or the like. In some cases, a performance plan calculation procedure includes transmitting installment information to the processor, and determining the performance plan based on the installment information. In some cases, a performance plan calculation procedure includes transmitting building information to the processor, and determining the performance plan based on the building information. A performance plan calculation procedure may include transmitting target information to the processor, and determining the performance plan based on the target information.

In still another aspect, embodiments of the present invention provide a computer program product for evaluating a performance installment in a building construction. The computer program can include code for receiving a first analysis information associated with the building construction prior to implementation of the performance installment, code for receiving a second analysis information associated with the building construction subsequent to implementation of the performance installment, and code for evaluating the performance installment based on a comparison of the first analysis information and the second analysis information. The computer program product may also include code for determining whether the performance installment meets a requirement of an energy guarantee program. In some cases, the computer program product includes code for determining whether the performance installment meets target information. The computer program product can include code for creating a map of the building construction. In some aspects, the map includes an image of the building construction prior to implementation of the performance installment, an image of the building construction subsequent to implementation of the performance installment, or both. A computer program product may also include code for calculating a performance plan based on the second analysis information. In some embodiments, a computer program product includes code for calculating an energy savings based on a comparison of the first analysis information and the second analysis information.

For a fuller understanding of the nature and advantages of the present invention, reference should be had to the ensuing detailed description taken in conjunction with the accompanying drawings.

DETAILED DESCRIPTION OF THE INVENTION

Embodiments of the present invention provide imaging techniques to accurately map areas of a building both before and after implementing performance measures such as weatherization or comfortization installments. Often, such imaging involves thermal or infrared technology. In the case of drill and fill insulation procedures, maps can be used to evaluate whether the desired cavities were filled, to determine if any unwanted voids or compressions are present, and to check that the desired level of thermal performance was achieved.

A portable thermal imaging camera can be used to capture the heat loss (winter) or heat gain (summer) signatures on one or more sections of a building structure or construction. This information can be downloaded to a computer containing mapping software which can be used to develop a detailed structural map of the building along with the calculated amount of insulation required in each cavity of the building. The map can also show installers where air sealing is needed or desirable. At the completion of the insulation installation job, the thermal imaging can be repeated to ensure that all desired cavities were filled, that no undesired voids are present, and that the desired level of thermal performance is achieved. The before and after images or maps can be used to estimate the energy savings potential of the retrofit work as part of an energy guarantee program.

Thermal imaging techniques can be used in a variety of different climate areas and during most if not all seasons of the year. It is often useful to conduct imaging when there is a reasonable temperature difference between the interior of the building or structure and the outside ambient conditions so that heat flow through the structure is facilitated. In summer, such a temperature difference would exist if, for example, the building interior were air conditioned to about 70 degrees F. and the outside air was about 80 degrees F. or higher. In winter, such a temperature difference would exist if, for example, the building interior were heated to about 70 degrees F. and the outside air was about 50 degrees F. or less. These and other types of temperature differences allow heat flow to be imaged.

Figure 1A:
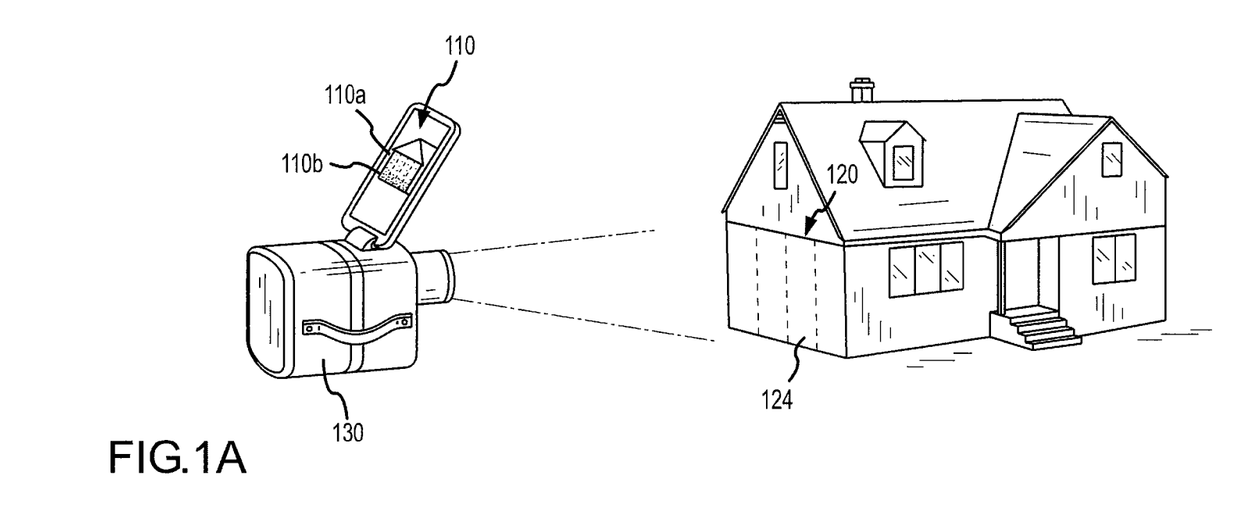
FIGS. 1A-E depict aspects of a method and system for evaluating a performance installment in a building construction, according to embodiments of the present invention.

Turning now to the drawings, FIGS. 1A-1E illustrates a method of evaluating a weatherization or performance installment in a building construction, according to embodiments of the present invention. As shown in FIG. 1A, the method can include preparing a first image 110 of a building construction 120 such as a wall of a house. Typically, an imaging device 130 is used to prepare image 110 or otherwise collect data that can be processed to create image 110. In some cases, the camera can be used to capture a heat loss signature (e.g. during the winter). Optionally, the camera can be used to capture a heat gain signature (e.g. during the summer). Signatures may be captured from one or more sections of a building construction such as a wall. A wide variety of imaging devices can be used to collect thermal signature data or information. These techniques can incorporate thermal modeling and analysis programs implemented by a computer. In some embodiments, image data is collected with a thermographic camera or sensor. The camera or sensor may be portable. Such devices, which include forward looking and other infrared cameras, can use infrared radiation to form an image or data that characterizes a thermal signature. Thermographic cameras include those having cooled infrared image detectors, those having uncooled detectors, and any other suitable camera for sensing a thermal signature. Sensing devices or systems may also include spot radiometers, point radiometers, thermal line scanners, and the like. Thermographic analysis may also incorporate blower door procedures which amplify or exaggerate air leakages in a building shell or envelope. As seen in FIG. 1A, first image 110 includes bright portions 110a indicating warm temperatures and dim portions 110b that indicate cool temperatures. If the image were captured of an exterior surface 124 or other portion of wall 120 from a location outside of the house on a cold day during the winter, it would likely indicate that adequate insulation is present in those portions of the wall corresponding to the dim portions of the image, and that inadequate insulation is present in those portions of the wall corresponding to the bright portions of the image. In some embodiments, the brightest parts of the image are white and correspond to warm temperatures, the dimmest parts of the image are black and correspond to cold temperatures, and other parts are red and yellow and correspond to intermediate temperatures. In some cases, the image or data represents an R (Resistance) value or R-value profile for the building construction. R-values and other metrics can be used to characterize heat flow properties.

The observed thermographic signature for the building construction may be deficient for any of a variety of reasons. In some cases, for example, loose-fill insulation can lose its installed R-value because of settling, especially in attic cavities. Some materials may settle more than others. For example, cellulose often settles more than rock wool or fiberglass. If the density of the insulation is too low, or if a particular cavity is not completely or sufficiently filled, voids or gaps can occur. In some cases, an installation material may have been fluffed during installation such that it meets a minimum thickness level but not a minimum weight requirement. The thermographic signature data can be used in any of a variety of ways. Signature data can be input into a computer in digital or analog form, and the computer software program can be configured to calculate a set of treatment parameters for a performance installment based on the data. A set of treatment parameters can include variables such as a thermal insulation location, a thermal insulation density, a thermal insulation amount, an air sealing location, an acoustic installment location, a vibrational installment location, and the like. For example, it is possible to download such data to a computer that contains mapping software, and then use the computer to develop a detailed structural map of the building along with the calculated amount of insulation required in each cavity of the building. The map can also indicate where air sealing is needed or desirable. These treatment parameters can also be part of a performance plan, as further described below.

Figure 1B:
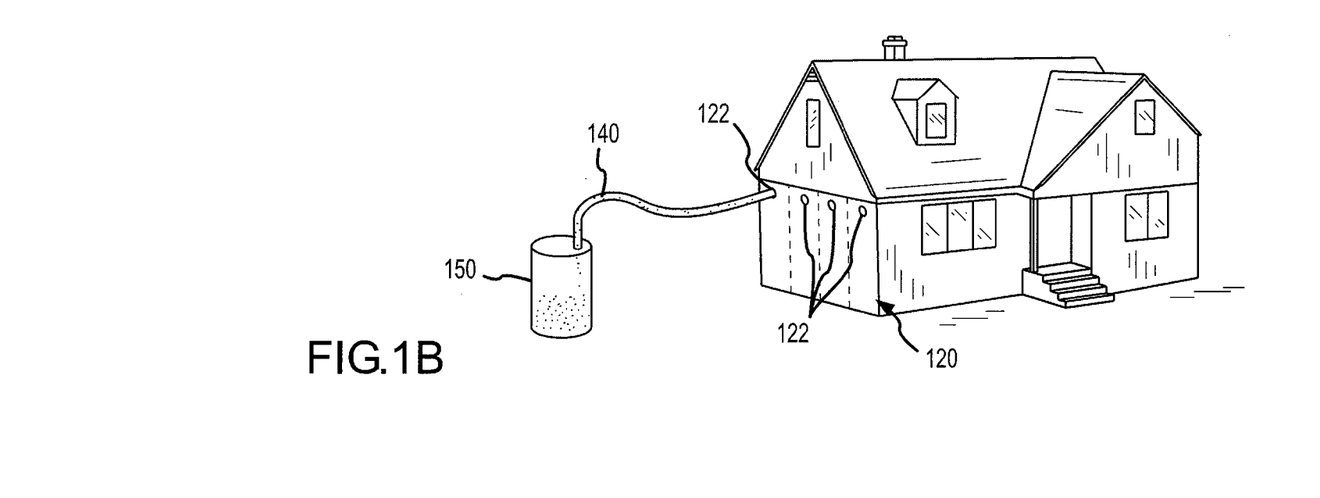

The method can also include performing a weatherization or performance installment in a building construction. For example, as illustrated in FIG. 1B, the method can include adding insulation to a house wall by a drill and fill technique, whereby insulation material 140 is applied to building construction 120 via an aperture or passage 122 in the construction. Application holes 122 or slots are usually drilled or cut through the exterior siding or sheathing material, or both. In some cases, application holes are drilled through the interior wallboard. These holes can be drilled with, for example, a 2½" to 4" diameter hole saw. Loose-fill insulation or foam insulation 140 can be pneumatically pumped with an insulation application device 150 into construction cavities via the entry hole. In some cases, insulation 140 is applied until a desired density of insulation, or a particular R-value, is reached. After the cavity is filled or the insulation is otherwise installed, the hole is plugged in a manner to allow for texturing and painting. The size of the entry hole is often determined by the diameter of the insulation application hose or application device and any additional area desired to bleed off unwanted or excessive air pressure during the filling process. In some cases, imaging or sensing techniques can be used to verify that the desired level of insulation is present in the cavity prior to closing the access drill hole.

Figure 1C:
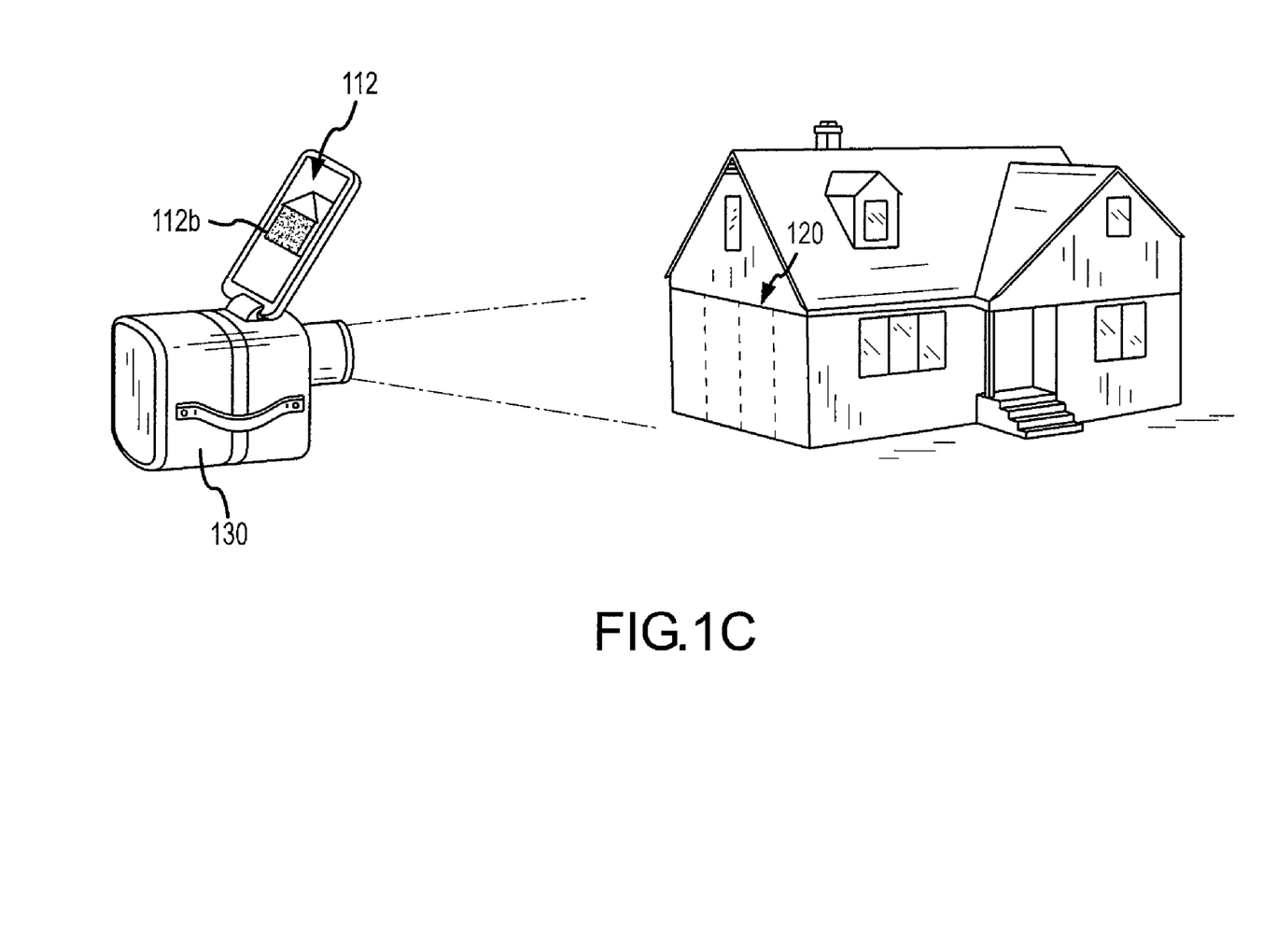

As shown in FIG. 1C, the method can further include preparing a second image 112 of a building construction 120 such as a wall of a house. Typically, imaging device 130 is used to prepare image 112 or otherwise collect data that can be processed to create image 112. As seen here, second image 112 includes primarily dim portions 112b that indicate cool temperatures. If the image were captured from a location outside of the house on a cold day during the winter, it would likely indicate that adequate insulation is present in most or all portions of the wall.

Figure 1D:
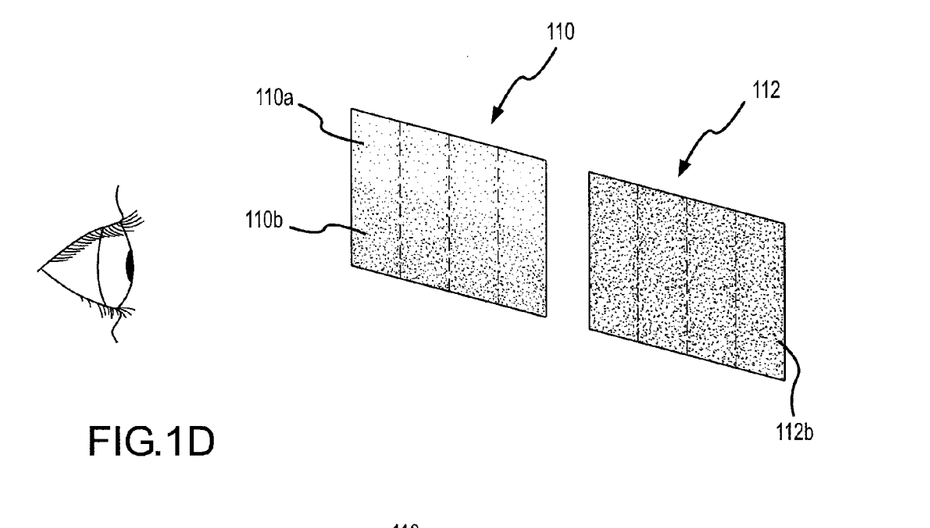

Given first image 110 and second image 112, it is possible to evaluate the drill and fill weatherization installment, by comparing the images or data or information associated with the images. For example, as shown in FIG. 1D, it is possible to evaluate the weatherization installment by visually comparing images 110 and 112. In this example, the viewer can see that first image 110 contains bright portions 110a and dim portions 110b, whereas second image 112 contains primarily dim portions 112b. Based on this comparison, it is possible to determine, estimate, conclude, or otherwise form the mental impression that the weatherization installment reduced the amount of heat present on the exterior 124 of the wall 120 corresponding to portions 110a or the amount of heat escaping from those portions of wall 120.

Figure 1E:
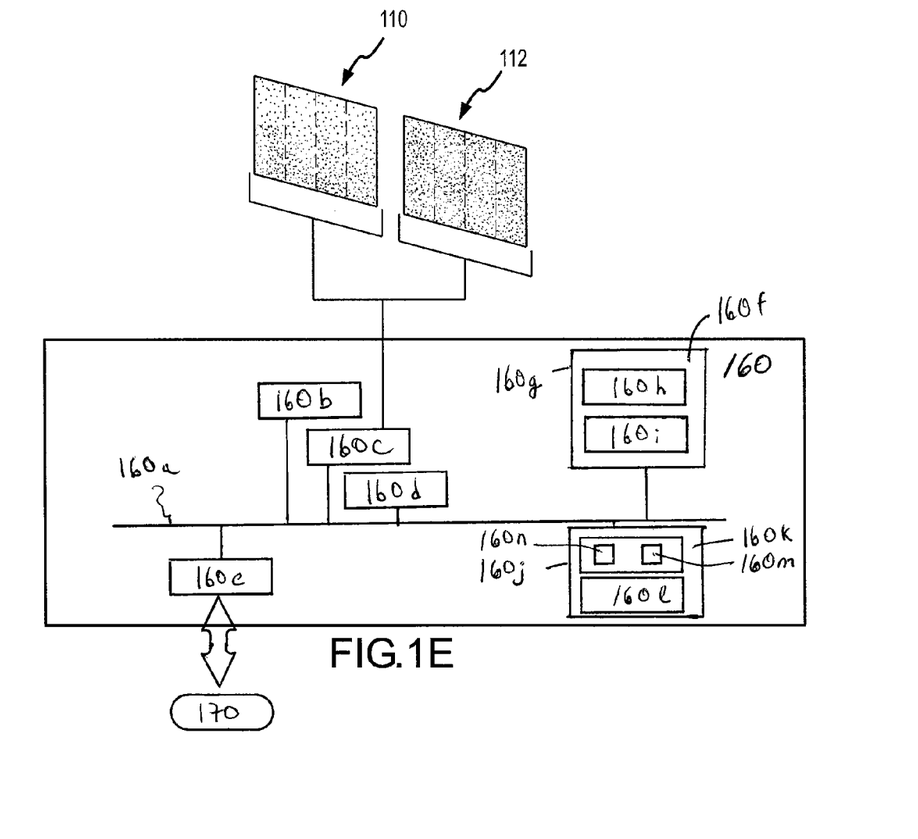

At the completion of an insulation installation job, the thermal imaging can be repeated to ensure that all desired cavities were filled, that no undesired voids are present, and that the desired level of thermal performance is achieved. For example, as depicted in FIG. 1E, it is possible to evaluate the drill and fill weatherization installment by comparing thermographic images or other data using a computational device. In such embodiments, images 110 and 112, data or information associated with or characterizing the images, data or information associated with thermal signatures, and the like, can be input into a computer or processor. A computer system 160 can be configured to calculate a performance installment based on the thermal signature data and other variables. As shown here, computer system 160 is shown comprised of hardware elements that are electrically coupled via a bus or bus subsystem 160a, including one or more processors 160b, one or more input devices 160c such as user interface input devices, one or more output devices 160d such as user interface output devices, and an interface subsystem 160e. System 160 can be configured to provide connectivity with a communication network 170. For example, interface subsystem 10e can be configured for wired or wireless communication with network 170. In some embodiments system 160 also comprises software elements, shown as being currently located within working memory 160f of memory 160g, including an operating system 160h and other code 160i, such as a program designed to implement methods of the invention.

Likewise, in some embodiments system 160 may also include a storage subsystem 160j that can store the basic programming and data constructs that provide the functionality of the various embodiments of the present invention. For example, software modules implementing the functionality of the methods of the present invention, as described herein, may be stored in storage subsystem 160j. These software modules are generally executed by the one or more processors 160b. In a distributed environment, the software modules may be stored on a plurality of computer systems and executed by processors of the plurality of computer systems. Storage subsystem 160j can include memory subsystem 160k and file storage subsystem 160l. Memory subsystem 160k may include a number of memories including a main random access memory (RAM) 160m for storage of instructions and data during program execution and a read only memory (ROM) 160n in which fixed instructions are stored. File storage subsystem 160l can provide persistent (non-volatile) storage for program and data files, and may include tangible storage media which may optionally embody installment information, analysis information, building information, target information, and the like. File storage subsystem 160l may include a hard disk drive, a floppy disk drive along with associated removable media, a Compact Digital Read Only Memory (CD-ROM) drive, an optical drive, DVD, CD-R, CD-RW, solid-state removable memory, other removable media cartridges or disks, and the like. One or more of the drives may be located at remote locations on other connected computers at other sites coupled to system 160. The modules implementing the functionality of the present invention may be stored by file storage subsystem 160l.

The system may be configured to include or execute a computer program product for evaluating a performance installment in a building construction, based on a comparison between a first image of the building construction captured prior to the performance installment, and a second image of the building construction captured subsequent to the performance installment. The program product can include code for receiving a first image, code for receiving the second image, and code for evaluating the installment based on a comparison between the first image and the second image. The program product may also include a computer-readable medium for storing the codes.

It is appreciated that system 160 can be configured to carry out various methods of the present invention. For example, processor component or module 160b can be a microprocessor control module configured to receive signals from input device or module 160c, and transmit signals to output device or module 160d and/or interface device or module 160e. Each of the devices or modules of the present invention can include software modules on a computer readable medium that is processed by a processor, hardware modules, or any combination thereof. Any of a variety of commonly used platforms, such as Windows, Macintosh, and Unix, along with any of a variety of commonly used programming languages, may be used to implement the present invention.

User interface input devices 160c may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 160c may also download a computer executable code from a tangible storage media or from a communication network, the code embodying any of the methods of the present invention. It will be appreciated that system software may be updated from time to time and downloaded to the system as appropriate. In general, use of the term "input device" is intended to include a variety of conventional and proprietary devices and ways to input information into system 160.

User interface output devices 160c may include, for example, a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 160 to a user.

Bus subsystem 160a provides a mechanism for letting the various components and subsystems of system 160 communicate with each other as intended. The various subsystems and components of system 160 need not be at the same physical location but may be distributed at various locations within a distributed network. Although bus subsystem 160a is shown schematically as a single bus, alternate embodiments of the bus subsystem may utilize multiple busses.

It will be apparent to those skilled in the art that substantial variations may be used in accordance with specific requirements. For example, customized hardware might also be used and/or particular elements might be implemented in hardware, software (including portable software, such as applets), or both. Further, connection to other computing devices such as network input/output devices may be employed. System 160 itself can be of varying types including a computer terminal, a personal computer, a portable computer, a workstation, a network computer, or any other data processing system. Due to the ever-changing nature of computers and networks, the description of system 160 depicted in FIG. 1E is intended only as a specific example for purposes of illustrating one embodiment of the present invention. Many other configurations of system 160 are possible having more or less components than the computer system depicted in FIG. 1E. Relatedly, any of the hardware and software components discusses above can be integrated with or configured to interface with other components of the sheet processing system.

Images or data can be used to estimate the energy savings potential of the retrofit work. In some embodiments, before or after images or maps can be used as part of an energy guarantee program. Energy guarantee programs often include an assurance from an installer or contractor that a building or home will provide a certain level of energy efficiency, or that its heating and cooling energy usage will not exceed a certain level. For example, an insulation installer may guarantee that a home will not use more than a specified amount of heating or cooling energy, or that the utility bill for heating or cooling a building will not exceed a certain amount. If such amounts are exceeded, the installer may reimburse the homeowner a percentage of the overage. Evaluation methods provided by embodiments of the present invention can be used to evaluate whether a building or home is eligible for an energy guarantee program. Thus, these techniques are well suited for providing or supporting energy savings guarantees. Relatedly, before or after images or maps can be used as part of an energy efficiency certification or program such as the Colorado Built Green® label or the EPA's Energy Star Home qualification. For example, a home registered with the Built Green® program must meet certain energy efficiency requirements. Imaging maps or data, as described herein, can be used to validate the eligibility of a building for such a certification or program.

Figure 2A:
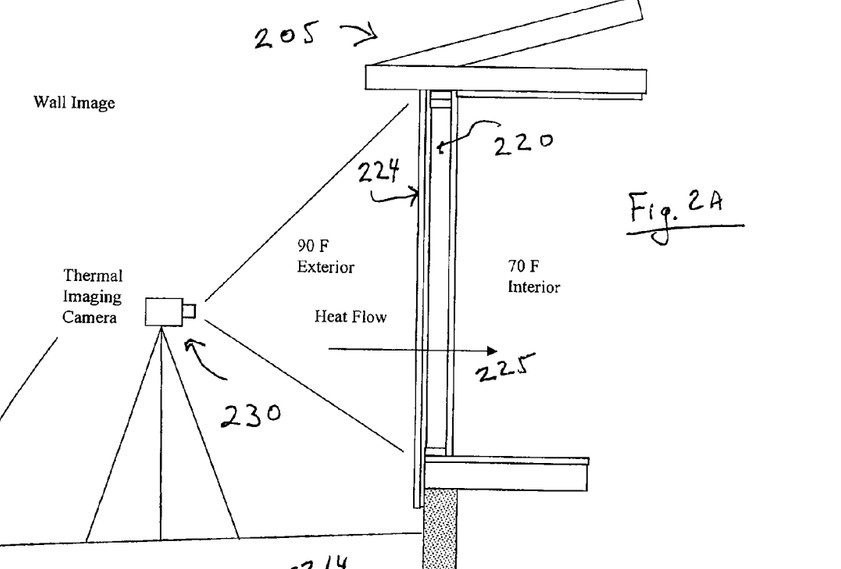
FIGS. 2A-C illustrate aspects of a performance analysis procedure according to embodiments of the present invention.
Figure 2B:
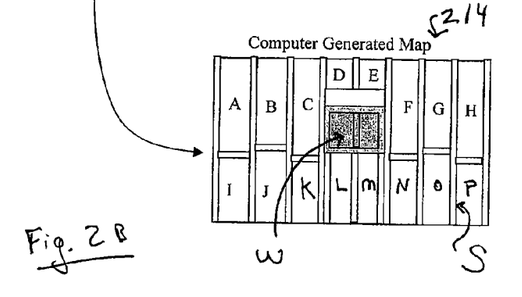
Figure 2C:
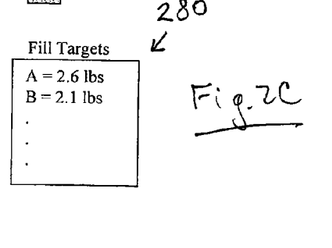

FIGS. 2A-C illustrate aspects of a weatherization analysis procedure according to embodiments of the present invention. FIG. 2A depicts a thermographic imaging camera 230 that is used to capture a thermographic profile or image of a wall 220 of a building 205. In this example, the exterior of the building is 90 degrees F. and the interior of the building is 70 degrees F., resulting in a heat flow from the exterior to the interior, as indicated by arrow 225. Based on the data or information collected by camera 230, it is possible to prepare a computer generated map 214 that reflects the thermographic signature of wall 220. Map 214 includes the thermographic profile of cavities A-P within wall 220, as well as the thermographic status of studs S and window W. In some cases, it is possible to utilize fill target data 280 when determining the thermal deficiency of a building construction or when determining how much insulation to apply to the building construction, as a treatment parameter or as part of a performance plan or installment. For example, an installer may determine that based on map 214, cavity A contains 2.4 lbs of insulation. The installer can consult fill target data 280, which suggests a fill target of 2.6 lbs for cavity A. The installer then determines that an additional 0.2 lbs of insulation is needed to increase the amount of insulation in cavity A to the suggested fill target. In some embodiments, data associated with wall 220 can be input into a computer configured for calculating aspects of a performance plan, which may include a weatherization plan or a comfortization plan. An exemplary computer program product for calculating a performance plan for a building construction can include code for receiving analysis information related to the building construction, and code for determining the performance plan based on the analysis information. The computer program product may also include code for determining the performance plan based on installment information, code for determining the performance plan based on building information, code for determining the performance plan based on target information, and the like.

Thermographic data can also be used by the installer, or evaluated by a computer, when determining or calculating where to drill a hole for the application of thermal insulation. In some situations, an installer may not have architectural or building plans for a wall or other building construction, and therefore may not be certain of the location or existence of cavities within the wall. Often, a thermographic image can provide the installer with such information. For example, the installer can consult thermographic map 214 which is helpful in depicting the locations and dimensions of cavities within the wall. Thermal images or maps can be prepared both prior to and subsequent to installation of a weatherization measure. This information can be presented to a homeowner or otherwise viewed or analyzed to demonstrate the resultant heat flow reduction afforded by the weatherization measure.

Figure 3:
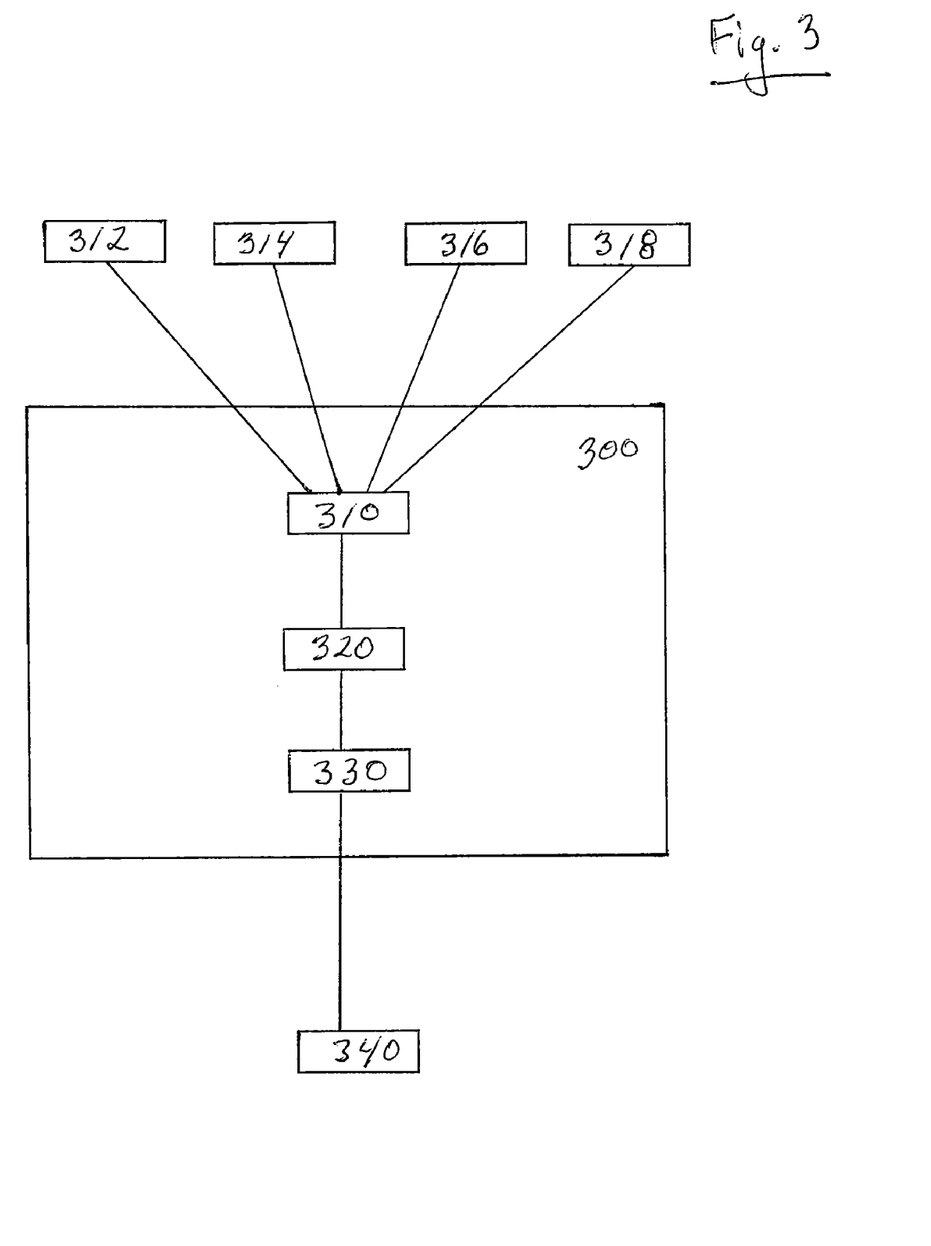
FIG. 3 shows a computer system for calculating a performance plan according to embodiments of the present invention.

FIG. 3 illustrates a computer system 300 according to embodiments of the present invention. System 300 includes an input 310 for receiving a variety of data or information related to weatherization or comfortization aspects of a building or home. For example, input 310 can receive installment information 312 pertaining to materials and labor involved with installing a weatherization or comfortization measure. Installment information 312 can include lists and descriptions of materials that can be used as part of a weatherization or comfortization installment, such as thermal insulation, air sealing materials, acoustic panels, vibration dampeners, and the like. Installment information 312 can also include the retail or wholesale cost for such materials, as well as data related to labor costs for installing the materials. Installment information 312 can include data regarding contractors for implementing weatherization or comfortization measures. This data can reflect the availability, reliability, efficiency, specialization, and other aspects of the contractors. In some cases, installment information 312 includes detailed information regarding structural, functional, and other aspects of weatherization and comfortization materials. Installment information 312 may include density, weight, availability, installation restrictions or guidelines, and other data associated with a particular thermal insulation material. For example, installment information 312 may include thickness recommendations or information related to settling properties of a loose-fill insulation material. Input 310 can also receive analysis information 314 pertaining to thermal, acoustic, vibrational, or airflow characteristics of a building or building structure. Analysis information 314 can include thermal signatures, acoustic signatures, vibrational signatures, airflow signatures, and the like, or any desired combination thereof. Analysis information 314 can include a single signature, multiple signatures, signatures that represent a specific time point, or signatures that represent multiple points in time. In an exemplary embodiment, analysis information 314 includes a first thermal signature of a building construction prior to implementation of a weatherization or comfortization installment, and a second thermal signature of a building construction subsequent to implementation of the installment.

As further shown in FIG. 3, input 310 can receive building information 316 pertaining to the actual construction or features of a particular building or home. Building information 316 can include architectural or blueprint information that reflects dimensions, locations, or other features of walls, crawlspaces, attics, floors, or cavities within the building. For example, building 316 may indicate that a particular wall in a building includes 10 cavities, each having a height of 9 feet, a width of 24 inches, and a depth of 4 inches. Building information 316 may also include lists and descriptions of materials in existing weatherization or comfortization features in a building. For example, building information 316 may include data regarding thermal insulation, air sealing materials, acoustic panels, vibration dampeners, and the like, that are present in the building. Building information 316 may indicate the location or amount of a particular weatherization or comfortization feature in a building. In some cases, building information 316 includes detailed information regarding structural, functional, and other aspects of weatherization and comfortization materials that are in the building. For example, building information 316 may include density, weight, R-value, and other data associated with a particular thermal insulation material. Building information 316 can also include building dimensions, such as well lengths and heights, as well as the age, location, climate zone, orientation, and front azimuth of the building. In some cases, building information 316 includes data regarding utility providers and rate schedules.

What is more, input 310 can receive target information 318 pertaining to desired acoustic, vibrational, or airflow characteristics of a building or building structure. Target information 318 may include information that reflects desired thermal insulation parameters for walls, crawlspaces, attics, floors, or cavities within the building. For example, target information 318 may indicate that for a particular wall in a building the desired R-value is 20, or that for a particular cavity within a wall the desired insulation type is cellulose or the desired insulation density is 2 lb/ft$^3$. In some instances, target information 318 encompasses standards set forth or suggested by governmental or private entities. For example, target information 318 may indicate that the desired insulation density meets the standards set forth in a particular building or fire code. In some cases, target information 318 includes data related to a home energy rating system. Target information 318 may also include budgetary constraints or preferences of a builder, homeowner, installer, or the like.

In some embodiments, system 300 includes a processor 320 for generating a performance plan such as a weatherization plan or a comfortization plan. System 300 may also include an output 330 for transmitting, printing, or displaying the weatherization or comfortization plan 340. The plan 340 may printed, displayed on a graphic computer screen, or sent to another computer or system. Performance plan 340 may include a description of a performance measure, instructions for installing performance measure, and other parameters related to a performance measure or installment. For example, performance plan 340 may indicate what performance measure to apply to or install in a building or building construction, where to install the performance measure, how much or what amounts to install, and the like. Performance plan 340 may include graphics, text, maps, tables, instructions, installation restrictions, guidelines, and the like. It is appreciated that system 300 may include one or more system components or elements as described herein with reference to FIG. 1E. For example, system 300 may include a memory, a user interface input device, a bus, a network interface, a storage subsystem, and the like.

A builder, contractor, homeowner, or the like may wish to implement a performance plan by applying a performance installment to a building or home. The performance plan may be determined by system 300 based on a variety of data, including installment information, analysis information, building information, target information, and the like. A performance plan may include one or more treatment parameters as described elsewhere herein. In some cases, the performance plan may be calculated by optimizing one or more of these data or treatment parameters. For example, the performance plan may be optimized to provide a maximum energy efficiency rating, or a minimum materials cost. In some cases, a performance plan can be calculated with an optimization algorithm. For example, an optimization algorithm can be used to determine a performance plan that includes construction materials that are readily available to an installer. An algorithm can also generate assembly or installation instructions based on input data. Algorithms for optimizing performance plans may be included in or implemented by one or more modules of computer system 300. The modules may be software modules on a computer readable medium that is processed by processor 320, hardware modules, or a combination thereof. One or more modules may also include optimization algorithms for implementing methods of the present invention.

The thermographic, acoustic, and vibration techniques discussed herein can also be used to accurately map out areas of a building structure prior to installing insulation or performing any type of air sealing, housewrapping, or other weatherization or comfortization work. For example, a weatherization installer may use a thermographic image of a building as a guide when determining where to apply weatherization elements and in what amounts. In some cases, thermographic, acoustic, or vibration information is used on a real-time basis during the application of a weatherization or comfortization installment, such that the installer can verify the status of the procedure from one moment to the next.

As used herein, weatherization, weatherproofing, and comfortization are often interchangeable terms, as the installation of weatherization or weatherproofing measures often lead to improvements in the comfort of a building, and installation of comfortization measures similarly can lead to improvements in the weatherization properties of a building, such as the ability of a building to resist or withstand environmental influences such as sunlight, precipitation, wind, humidity, and temperature. In some embodiments, weatherization measures, weatherproofing measures, or comfortization measures may be referred to as performance measures. These measures can confer enhanced energy efficiency characteristics to a building, as well as improved air quality, airtightness, ventilation, and moisture control. Similarly, they may attenuate or dampen noise or vibrations from inside or outside the building. They often result in increased thermal uniformity and reduced temperature gradients. Weatherization or comfortization materials are often installed at the walls, ceilings, rafters, roofs, doors, windows, crawl spaces, floors, pipes, ducts, vents, joints, or seams of a building, or a combination of any of these building constructions.

One common weatherization measure involves the installation of thermal insulation. Typically, thermal insulation materials act to reduce the rate of heat transfer, and can include reflectors that reduce radiative heat transfer. Some insulation materials act to block or inhibit heat convection. Thermal insulators can also include foams or cellular, granular, or fibrous materials that reduce conductive heat transfer. Thermal insulation materials typically rely on heat-transfer resistance to impede heat transfer between the exterior and interior of a building, or between building constructions elements such as walls, ceilings, floors, and the like. Thermal insulation materials include substances that may not act as true insulators, but instead play a role in regulating temperature. For example, adobe, earth, stone, and concrete can modulate temperatures in a building by damping temperature fluctuations in the outdoor environment. Often, insulation will include materials having low thermal conductivity. In some cases, thermal insulators may include a combination of different types of thermal insulation materials. Exemplary insulation or weatherization materials or devices include radiant barriers, low emissivity windows, housewrap, foil-backed bubble pack and other foil products, reflective materials such as paint and shingles, batts, blankets, caulk, siding, wind-proof cladding, oriented strand board (OSB), sheathing, rock and slag wool, fiberglass, synthetic and natural fibers, loose fill materials, cellulose, spray foams, open cell foams, closed cell foams, polyurethane, rigid panels, structural insulating panels, aerogels, straw bales, and the like. Weatherization or comfortization measures can also involve the installation of air or vapor barriers. Air sealing methods or techniques can involve the application of caulk, spray foam, weather stripping, and the like, to air leaks at walls, windows, doors, attics, basements, crawlspaces, and other building constructions. Air leakages can be detected by any of a variety of devices or methods, including blower doors, duct blowers, manometers, flow hoods, infrared cameras, and the like. Installation of materials and devices that improve airtightness in a building or building construction can reduce the amount of heat that is lost by a building during the cold season, and the amount of heat that is gained by a building during the warm season.

Drill and fill techniques often involve the application of loose-fill insulation, which can include small particles of fiber, foam, cellulose, fiberglass, mineral wool, polystyrene beads, vermiculite, or perlite. Table 1 provides a comparison of common loose-fill materials, according to one embodiment of the present invention.

TABLE 1

| | Insulation | | | | | |
|---|---|---|---|---|---|---|
| | Cellulose | | Fiberglass | | Rock Wool | |
| | Application | | | | | |
| | Open Blow | Enclosed Cavity | Open Blow | Enclosed Cavity | Open Blow | Enclosed Cavity |
| R-value/inch | 3.2-3.7 | 3.2-3.6 | 2.0-3.0 | 3.2-4.2 | 3.0-3.3 | 3.3-3.6 |
| Density, lb/ft$^3$ | 1.5-2.0 | 2.2-3.5 | 0.5-1.0 | 0.8-2.0 | 1.6-2.5 | 2.0-3.0 |

In some situations, loose-fill insulation is installed in enclosed cavities, such as the spaces between framing studs on the interior of a wall. In other situations, loose-fill insulation can be installed in unenclosed spaces, such as in an attic. Installation may involve drilling one or more holes between the studs of a wall, and blowing insulation into a cavity between the studs with an insulation blower to achieve the desired insulation density, coverage, R-value, and the like. The installation holes can them be sealed.

In addition to providing improvements in energy efficiency, insulation materials that are used in homes and other buildings can absorb noise and vibration. Relatedly, embodiments of the present invention encompass methods that involve capturing data or information that characterizes acoustic or vibration signatures of a building, and performing a noise or vibration treatment installation in the building. The noise or vibration treatment may include installation of thermal insulation materials, acoustic insulation or soundproofing materials, vibration dampening materials, or any desired combination thereof. The methods can further include subsequently capturing post-treatment data. Such methods can also involve evaluating the noise or vibration treatment installation, which may also be referred to as or include a comfortization or weatherization installment, based on a comparison between the pre-treatment data and the post-treatment data. These methods are well suited for improving the acoustics of homes, buildings, music and opera performance halls, and the like. Similarly, they can be used to improve the vibrational characteristics of laboratories, manufacturing facilities, buildings, homes, and other structures where vibrations may be treated.

Suitable soundproofing materials include noise barriers which block or absorb the energy of sounds waves, damping structures such as sound baffles, anti-noise generators, acoustic panels, sound masking devices, noise control systems, and the like. These materials typically act to reduce or absorb noise. For example, materials that include layers having different densities, such as open cell foam, often provide desirable sound damping characteristics. Any of a variety of techniques or devices can be used to capture an acoustic map or visualize a sound field of a building or building construction. For example, a microphone array can detect an acoustic signature in a room. Acoustic holography provides another approach for characterizing an acoustic map. In some embodiments, these techniques incorporate acoustic modeling and analysis programs implemented by a computer.

Vibration damping devices or materials can be used to reduce or prevent the effects of vibrational stimuli such as wind, aircraft, railroad trains, vehicles, seismic events, cooling fans, refrigerators, HVAC systems, elevators, office machinery, and human or animal footfalls. Any of a variety of vibration testing techniques or devices can be used to prepare a vibration signature or map of a building or building construction, including stress testing, shock testing, vibration meters, and the like. Suitable vibration installments or treatments include baffles, barriers, dampers, isolators, sliders, and the like. In some embodiments, these techniques incorporate vibration modeling and analysis programs implemented by a computer.

Although certain system, device, and method embodiments have been disclosed herein, it will be apparent from the foregoing disclosure to those skilled in the art that variations, modifications, alternative constructions, and equivalents of such embodiments may be made without departing from the true spirit and scope of the invention. For example, the present invention encompasses systems which can carry out the methods described herein, and similarly encompasses methods for which the systems described herein may be used. Additionally, a number of well known processes and elements have not been described in order to avoid unnecessarily obscuring the present invention. For example, those skilled in the art know how to arrange computing devices into a network and configure communication among them. Accordingly, the above description should not be taken as limiting the scope of the invention, which is defined in the following claims.

What is claimed is:

1. A method of evaluating a performance installment in a building construction, comprising:
    preparing a first image of the building construction;
    implementing the performance installment in the building construction;
    preparing a second image of the building construction subsequent to or during implementation of the performance installment; and
    evaluating the performance installment based on a comparison between the first image and the second image.

2. The method according to claim 1, wherein the first image comprises a first thermal image and the second image comprises a second thermal image.

3. The method according to claim 1, wherein the first image represents a heat loss signature or a heat gain signature of the building construction.

4. The method according to claim 1, wherein the building construction comprises a member selected from the group consisting of an exterior wall, an interior wall, a ceiling, a floor, a roof, an attic, a rafter, a basement, and a crawlspace.

5. The method according to claim 1, wherein the performance installment comprises a member selected from the group consisting of a thermal insulation installment, an air sealing installment, an acoustic installment, and a vibrational installment.

6. The method according to claim 1, wherein evaluating the performance installment comprises inputting the first and second images into a computer and processing the first and second images with mapping software to provide a map of the building construction.

7. The method according to claim 1, further comprising inputting the first image into a computer and calculating a set of treatment parameters for the performance installment based on the first image.

8. The method according to claim 7, wherein the set of treatment parameters comprises a member selected from the group consisting of a thermal insulation location, a thermal insulation density, a thermal insulation amount, and an air sealing location.

9. The method according to claim 1, further comprising incorporating the performance installment evaluation into an energy guarantee program.

10. A method of calculating a performance plan for a building construction, comprising:
    capturing analysis information using a member selected from the group consisting of a thermal imaging device, an airflow detecting device, an acoustic detection device, and a vibration testing device;
    transmitting the analysis information to a processor; and
    determining the performance plan based on the analysis information, the performance plan comprising a member selected from the group consisting of a weatherization plan and a comfortization plan;
    wherein the analysis information comprises a member selected from the group consisting of a thermal signature, an airflow signature, an acoustic signature, and a vibrational signature.

11. The method according to claim 10, further comprising transmitting installment information to the processor, and determining the performance plan based on the installment information.

12. The method according to claim 10, further comprising transmitting building information to the processor, and determining the performance plan based on the building information.

13. The method according to claim 10, further comprising transmitting target information to the processor, and determining the performance plan based on the target information.

14. A computer program product stored on a non-transitory computer-readable storage medium for evaluating a performance installment in a building construction, the program product comprising:
    code stored on the non-transitory computer-readable storage medium for receiving a first analysis information associated with the building construction prior to implementation of the performance installment;
    code stored on the non-transitory computer-readable storage medium for receiving a second analysis information associated with the building construction subsequent to implementation of the performance installment; and code stored on the non-transitory computer-readable storage medium for evaluating the performance installment based on a comparison of the first analysis information and the second analysis information.

15. The computer program product according to claim 14, further comprising code for determining whether the performance installment meets a requirement of an energy guarantee program.

16. The computer program product according to claim 14, further comprising code for determining whether the performance installment meets a target information.

17. The computer program product according to claim 14, further comprising code for creating a map of the building construction.

18. The computer program product according to claim 17, wherein the map comprises an image of the building construction prior to implementation of the performance installment, an image of the building construction subsequent to implementation of the performance installment, or both.

19. The computer program product according to claim 14, further comprising code for calculating a performance plan based on the second analysis information.

20. The computer program product according to claim 14, further comprising code for calculating an energy savings based on a comparison of the first analysis information and the second analysis information.

* * * * *